United States Patent [19]

Nur et al.

[11] Patent Number: 6,121,232

[45] Date of Patent: *Sep. 19, 2000

[54] STABILIZED MIXTURE COMPRISING FIBRINOGEN

[75] Inventors: Israel Nur; Lilliana Bar, both of Rehovot, Israel; Oded Lieberman, Brussels, Belgium

[73] Assignee: Omrix Biopharmaceuticals SA, Brussels, Belgium

[*] Notice: This patent issued on a continued prosecution application filed under 37 CFR 1.53(d), and is subject to the twenty year patent term provisions of 35 U.S.C. 154(a)(2).

[21] Appl. No.: 08/797,328

[22] Filed: Feb. 10, 1997

[30] Foreign Application Priority Data

Jan. 31, 1997 [BE] Belgium ............................ 97101569

[51] Int. Cl.$^7$ .................................................. A61K 38/00
[52] U.S. Cl. ............................... 514/2; 514/12; 514/479; 514/529; 514/533; 530/350; 530/380; 530/381; 558/276
[58] Field of Search ..................... 514/2, 12, 479, 514/529, 533, 870, 927, 310; 530/350, 380, 381, 382; 558/276

[56] References Cited

U.S. PATENT DOCUMENTS

| | | | |
|---|---|---|---|
| 4,377,572 | 3/1983 | Schwarz et al. | 424/101 |
| 5,278,189 | 1/1994 | Rath et al. | 514/561 |
| 5,578,326 | 11/1996 | Weis-Fogh | 424/529 |

FOREIGN PATENT DOCUMENTS 94 22503  10/1994  WIPO.

OTHER PUBLICATIONS

A. Takada, et al., "Importance Of Lysine In The Regulation Of Plasma Proteases And Inhibitors", pp. 19–20, 1983.
C. Lentner: "Geigy Scientific Tables", 1981, Ciba–Geigy, Basel XP002034353212490, pp. 92–93; tables 2–4.

*Primary Examiner*—Paula K. Hutzell
*Assistant Examiner*—Minh-Tam Davis
*Attorney, Agent, or Firm*—Jacobson, Price, Holman & Stern, PLLC

[57] ABSTRACT

A stabilized solution of fibrinogen containing samples, in particular a stabilized solution of the biological active component (BAC) which is a solution of proteins derived from blood plasma comprising fibrinogen, tranexamic acid and arginine or lysine or mixtures or arginine and lysine, their pharmaceutically acceptable salts, as well as, optionally, substances forming a buffered solution in aqueous medium.

14 Claims, 1 Drawing Sheet

STABILIZED MIXTURE COMPRISING FIBRINOGEN

The invention pertains to a mixture comprising fibrinogen, particularly to a stabilized solution of Biological Active Component (BAC), a two component tissue glue comprising separately components A and B as well as a fibrin clot obtainable by mixing component A and component B.

Fibrinogen containing samples can be used for various applications, e. g. in two component tissue glues or fibrin glues.Biologically Active Component (BAC) is a viscous solution of proteins containing fibrinogen typically in amounts about 50 mg fibrinogen per ml, which has been derived from cryoprecipitation of plasma. Such BAC is described in WO 94/22503. Since procedures employed for virus inactivation and concentration result in an increase of proteolytic activity in the cryoprecipitate, stabilization of the final product with anti-proteolytic agents is required. Some of these proteolytic enzymes are in a zymogen (pro-enzyme) form and their activation is promoted by the minute amount of activated enzymes present in the cryoprecipitate. The temperature range employed during separation of the cryoprecipitate has been found to enhance the activation of precursors of proteolytic enzymes. This activation presumably takes place by a "cascade" sequence, whereby proteases activate the precursor forms of other proteolytic enzymes, including the generation of fibrinolytic plasmin from the precursor plasminogen. Inhibition of fibrinolysis and other proteolytic activity has been found to reduce the degradation of factor VIII and of other coagulative and adhesive proteins. It may occur that BAC coagulates spontaneously already after a storage for one day at 2–6° C. At lower temperatures this process is slower; following storage for several moths at −18° C., BAC without further treatment forms a solid clot after thawing and cannot be reconstituted. The same phenomenon has been observed with unpurified cryoprecipitate.

During the production process, plasminogen and other vitamin K dependent proteases are removed by aluminum hydroxide adsorption. However, some proteases are left in the final product.

It is desirable to stabilize fibrinogen comprised in a mixture, in particular a solution of BAC in order to ensure a save usage of the product when applied in clinical operations.

Surprisingly, this object is attained by a mixture comprising fibrinogen, 4-(aminomethyl)cyclohexane-carboxylic acid as well as arginine, lysine or combinations thereof. Preferably, the mixture is present as a solution of fibrinogen, tranexamic acid (4- (aminomethyl)-cyclohexane-carboxylic acid) as well as arginine, lysine or combinations thereof. In a preferred embodiment the invention comprises a solution of the biological active component (BAC) which has been stabilized with a combination of tranexamic acid its physiologically acceptable salts and arginine or lysine or combinations of lysine and arginine. Optionally, the solution is buffered to a physiological compatible pH value. Tranexamic acid is a protease inhibitor which scientific name is 4-(aminomethyl)cyclohexane-carboxylic acid. According to the invention a buffer containing glycine is preferred.

Figure 1:
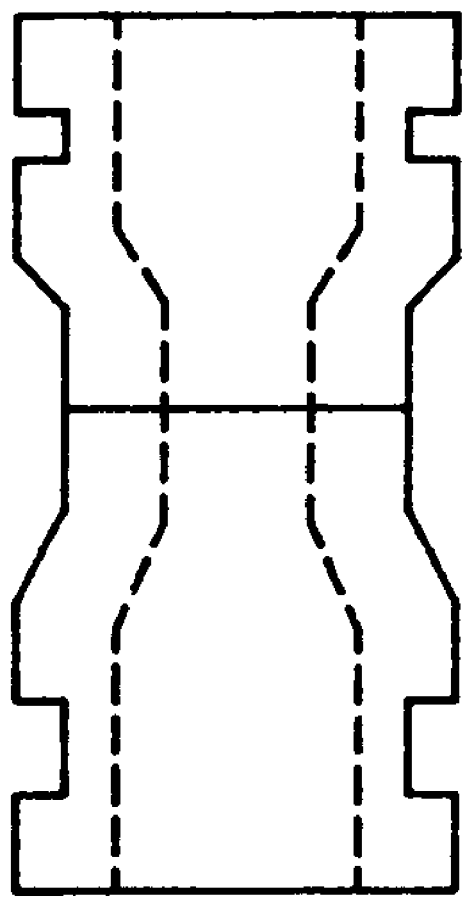
FIG. 1 is a side view of a cast designed to hold the liquid glue until it solidifies.

Arginine as well as lysine can be employed according to the invention as a common salt, for example, as hydrochloride. The BAC is preferably obtained from concentrated cryoprecipitate after being worked up as disclosed in EP-A-534 178. Arginine has been described in the art as a stabilizer in therapeutic protein concentrates. However, the synergistic effect provided by the combination of tranexamic acid and arginine as well as lysine is surprising.

Preferably, the amount of tranexamic acid in the solution of BAC is from about 1–20% by weight. The amount of arginine or lysine hydrochloride is preferably from about 0.1–4% by weight. More preferred are amounts of tranexamic acid of form about 5–15% by weight, particularly preferred from about 8–12% by weight. Typically about 10% by weight can be used. The amount of arginine or lysine hydrochloride is more preferred in the range of from about 1–3% by weight, in particularly preferred are about 2% by weight.

The fibrinogen comprising sample, in particular a solution of BAC, is preferably derived from a cryoprecipitate which was concentrated by ultra filtration as described in WO-A-94/22503. The BAC preferably comprises a fibrinogen content of from about 15–150 mg/ml in particular of from 20–80 mg/ml. The amount of fibrinogen can be measured according to Clauss' Method (Clauss, A., "Gerinnungsphysiologische Schnellmethode zur Bestimmung des Fibrinogens", Acta. Haematol., 17, 237–247, 1957).

The use of a BAC derived from concentrated cryoprecipitate is advantageous since such a fraction contains besides fibrinogen also valuable blood components which play an important role for blood-clotting when a proteolytic enzyme such as human thrombin is contacted with a BAC solution. Valuable components are factor VIII, factor XIII, fibronectin, vitronectin, von Willebrand factor (vWF), etc.

Preferably, the components are derived from cryoprecipitate, in particular concentrated cryoprecipitate. However, it is also possible that the components fibrinogen, factor VIII, factor XIII, fibronectin, von Willebrand factor (vWF), vitronection have been prepared by recombinant methods. Such preparations, for example, for factor VIII are commercially available.

It was found that the combination of tranexamic acid and arginine or lysine stabilizes a mixture containing fibrinogen in particular a solution of the biological active component BAC, (at 2–6° C. for at least 14 days by conserving at least 50% of the fibrinogen activity). When only one of the components was used, the sample was significantly more instable.

Furthermore, it was surprising that the use of tranexamic acid and arginine or lysine hydrochlride did not adversely effect properties of a blood clot obtained from BAC stabilized according to the invention. For example, the maximum elongation of the clot was maintained also after 14 days of storage of the respective samples as well as the tensile force was almost maintained on the same level. Also the factor VIII activity in the BAC was not negatively affected when tranexamic acid and arginine or lysine were added.

In particular, the stabilized solution of the biological active component BAC according to the invention is well suitable for the preparation of a two component tissue glue. A tissue glue according to the invention is understood as a system which can be applied with or on a patient in need thereof, for example, to avoid severe bleeding during surgical operations. The tissue glue is also addressed as fibrin glue and was basically analogous to the natural blood clotting cascade. The tissue glue is derived from two components prior to the application in surgical operations. One component contains fibrinogen which upon exposure to a proteolytic enzyme such as human thrombin forms fibrin which is the polymer forming the basic material of the natural blood clot. During surgical operations the two components are applied, for example, by two syringes which are emptied simultaneously by mixing the two components as fast as possible and avoiding the blockage of the supply lines. The solution according to the invention is advantageous for preparing a two component fibrin glue since the fibrinogen solution has not to be freshly prepared but can be stored in a refrigerator at −18° C., neither loosing its clotting ability nor its outstanding mechanical properties. The degrees of activity of fibrinogen can be balanced by providing a higher amount of fibrinogen in the solution so that the proper use of the fibrinogen containing solution (BAC) is not hampered.

Therefore, subject of the present invention is also a two component tissue glue comprising separately components A and B wherein component A comprises a solution according to the embodiments described in claims 1 to 10 and a component B comprising a solution of a proteolytic enzyme which is capable to react with fibrinogen (or BAC respectively) to form fibrin.

Preferably, the proteolytic enzyme is human thrombin in particular having an activity of from about 2 to 4,000 IU/ml. The activity of thrombin is measured according to the clotting assay (European Pharmacopoeia). It is understood by the skilled person that a fibrin glue may be defined by its content of clottable protein instead of the definition based on clottable fibrinogen.

In order to provide a balanced solution of the mixed components A and B it can be advantageous to add to component B approximately the same concentration of tranexamic acid and arginine.

Preferably, the components A and B are applied in such a way that equal volumes of the two components are mixed and applied onto the patient at the side of the respective wound. Of course, it is to be understood that the two component tissue glue can be employed not only during surgical operations but also in other situations where bleeding must be stopped. The two components are preferably applied in a ratio of 1:1.

The following examples illustrate the advantages of the stabilizing combination of tranexamic acid and arginine. These examples are by no means limiting but explain the invention in greater detail.

Example 1

Preparation of Test Substance

To 800 ml of a sample 0.8 g of sodium azide (0.1%) will be added as a powder to the bulk to control bacterial growth, immediately after receiving the sample from the production line. The addition of a bacteriostat is necessary to prevent contamination since high concentration of fibrinogen in sample is difficult to filtrate.

Each concentration tested will be prepared extemporaneously by addition of a mixture of the two solid components to a 100 ml aliquot of the sample. The addition of tranexamic acid and arginine-HCl will be performed in a beaker with moderate stirring (multipoint magnetic stirring plate) for 10 minutes. All formulations tested will be prepared in parallel and their fibrinogen concentration will be adjusted to 50 mg/ml by addition of buffer B.

| Group No. | BAC (ml) | Tranexamic Acid (g) | Arginine (g) | Buffer B (ml) | Final vol. (ml) |
|---|---|---|---|---|---|
| A | 100 | 0 | 0 | 20 | 120 |
| B | 100 | 0 | 2.4 | 17.6 | 120 |
| C | 100 | 6 | 2.4 | 11.6 | 120 |
| D | 100 | 12 | 2.4 | 5.6 | 120 |
| E | 100 | 12 | 0 | 8 | 120 |
| F | 100 | 12 | 1.2 | 6.8 | 120 |
| G | 100 | 12 | 4.8 | 3.2 | 120 |

After an additional 5 minutes stirring, 10 ml siliconized glass vials will be filled with 5 ml aliquots. All vials will be frozen simultaneously and stored at −80° C. until used. Before experiment, they will be placed at a temperature of 2–6° C. (day "0", base-line time).

Two vails from each group will be kept at −80° C. as positive controls. All experiments will be performed in duplicates and the vials will be labelled according to stabilizer concentrations as follows:

GROUP A: no stabilizer-vials $A_1$–$A_{20}$
GROUP B: 0% tranexamic acid and 2% arginine monohydrochloride-vials $B_1$–$B_{20}$
GROUP C: 5% tranexamic acid and 2% arginine monohydrochloride-vials $C_1$–$C_{20}$
GROUP D: 10% tranexamic acid and 2% arginine monohydrochloride-vials $D_1$–$D_{20}$
GROUP E: 10% tranexamic acid and 0% arginine monohydrochloride-vials $E_1$–$E_{20}$
GROUP F: 10% tranexamic acid and 1% arginine monohydrochloride-vials $F_1$–$F_{20}$
GROUP G: 10% tranexamic acid and 4% arginine monohydrochloride-vials $G_1$–$G_{20}$ Extra quantities of sample will be held as retention samples and used if needed.

Before testing all −80° C. frozen vials will be thawed at 37° C. for 15 minutes and placed at 2–6° C. (day "0"). Two vials from each group will be rolled at room temperature for 15 minutes at day 0 and their mechanical properties and biochemical tests will be performed and evaluated. The same procedure will be repeated on days 2, 4, 7, 9, 11, 14 and 30.

Mechanical Properties

Elongation test of fibrin glue will be done in a tensile Imachine CHATILLON MODEL TCD-200 with a CHATILLON Force Gauge of 1,000 g. Data will be handled by a computer program.

This instrument is a motor-driven tension and compression tester designed for testing the resilience, yield pints and breaking strengths of various products and materials.

In order to produce standardized clots of solidified glue in a form which could easily be attached to the tension testing machine, a special cast was designed. This consists of two conical aluminum moulds, each of 2.5 cm in height, which are placed one on top of the other (see FIG. 1). The liquid components of the glue are injected into the cast where they solidify into a standard clot of 12.7 mm×5 mm.

The casts are then anchored to the tension testing machine, and the tensile strength and the elongation of the cylinder of glue within the cast measured by pulling the two casts apart.

A computer program monitors the tensile force and elongation every 0.2 s. The points are plotted graphically on two axes: elongation versus force in grams at a given time.

Test Procedure

Vials containing BAC were incubated at 37° C. for 15 minutes and then rolled at room temperature for 15 minutes.

Custom designed aluminum casts (as previously described) were filled with a combined solution of 0.5 ml of BAC and 0.5 ml of thrombin (8 IU/ml).

The casts were left a room temperature for 45 minutes to allow the glue to solidify, and then mounted onto the gauge and the resultant clots tested for maximum elongation capacity and tensile strength (tensile force required to break the clot).

Biochemical Tests Performed

The following proteins were tested for their stability by the methods described:

Fibrinogen clotting activity: Fibrinogen was measured quantitatively by the clotting method according to Clauss.

EXAMPLE 2

The Effect of Various Concentrations of Tranexamic Acid and Arginine-HCl on the force/mm (slope) of the clot

| | Group A | Group B | Group C | Group D | Group E | Group F | Group G |
|---|---|---|---|---|---|---|---|
| | 0% TEA 0% Arg. | 0% TEA 2% Arg. | 5% TEA 2% Arg. | 10% TEA 2% Arg. | 10% TEA 0% Arg. | 10% TEA 1% Arg. | 10% TEA 4% Arg. |
| incubation days | | | | | | | |
| 0 | 2.34 | 3.55 | 3.49 | 3.1 | 3.92 | 3.26 | 0.68 |
| 1 | 0.9 | 1.9 | 3.3 | 3.17 | 3.4 | 3.2 | 1.83 |
| 4 | 0.5 | 1.13 | 3.24 | 3.02 | 3.49 | 3.17 | 1.3 |
| 7 | | | 2.95 | 2.79 | 3.49 | 3.12 | 1.75 |
| 9 | | | 2.92 | 2.71 | 3.37 | 3.21 | 1.54 |
| 11 | | | 2.94 | 2.73 | 3.34 | 3.19 | 1.16 |
| 14 | | | 2.86 | 2.82 | 3.37 | 3.08 | |

Conclusion: At freezing either Arg. or TEA enhance the slope of the clot (the clot is stronger than without stabilizers but TEA has stabilizing effect in the strength of the clot with time when incubating at 4–8° C.

EXAMPLE 3

The Effect of Various Concentrations of Tranexamic Acid and Arginine-HCl on the Content of Clottable Fibrinogen

| | Group A | Group B | Group C | Group D | Group E | Group F | Group G |
|---|---|---|---|---|---|---|---|
| | 0% TEA 0% Arg. | 0% TEA 2% Arg. | 5% TEA 2% Arg. | 10% TEA 2% Arg. | 10% TEA 0% Arg. | 10% TEA 1% Arg. | 10% TEA 4% Arg. |
| storage at -70° C. | 31.96 | 37.22 | 41.18 | 40.91 | 41.79 | 42.21 | 39.46 |
| incubation days | | | | | | | |
| 0 | 35.2 | 34.01 | 40.92 | 45.46 | 40.99 | 43.61 | 41.65 |
| 1 | 26.23 | 32.77 | 41.38 | 41.61 | 39.82 | 40.47 | 39.2 |
| 4 | 22.5 | 21.41 | 42.03 | 41.02 | 37.08 | 39.56 | 40.46 |
| 7 | 24.7 | 18.07 | 37.98 | 42.25 | 41.04 | 40.04 | 38.5 |
| 9 | 23.37 | 18.4 | 39.61 | 40.47 | 39.28 | 37.02 | 37.61 |
| 11 | 20.16 | 12.58 | 37.82 | 39.39 | 37.73 | 39.46 | 37.28 |
| 14 | 23.91 | 15.31 | 39.32 | 39.38 | 40.49 | 38.43 | 40.79 |
| 30 | 22.13 | 13.24 | 35.24 | 39.13 | 40.47 | 39.53 | 37.15 |

Conclusion: TEA stabilizes clottable fibrinogen

EXAMPLE 4

The Effect of Various Concentrations of Tranexamic Acid and Arginine-HCl on Factor VIII Activity

| | Group A | Group B | Group C | Group D | Group E | Group F | Group G |
|---|---|---|---|---|---|---|---|
| | 0% TEA 0% Arg. | 0% TEA 2% Arg. | 5% TEA 2% Arg. | 10% TEA 2% Arg. | 10% TEA 0% Arg. | 10% TEA 1% Arg. | 10% TEA 4% Arg. |
| storage at -70° C. | 9.13 | 11.15 | 13.98 | 15.26 | 12.87 | 13.51 | 14.23 |
| incubation days | | | | | | | |
| 0 | 8.77 | 9.19 | 11.22 | 11.87 | 8.42 | 10.52 | 10.67 |
| 1 | 6.54 | 3.38 | 9.79 | 10.15 | 8.91 | 8.11 | 6.85 |
| 4 | 4.78 | 6.32 | 9.16 | 10.28 | 8.68 | 8.93 | 9.15 |

EXAMPLE 4-continued

The Effect of Various Concentrations of Tranexamic Acid and Arginine-HCl on Factor VIII Activity

|    | Group A | Group B | Group C | Group D | Group E | Group F | Group G |
|----|---------|---------|---------|---------|---------|---------|---------|
| 7  | 6.19    | 5.61    | 8.98    | 11.31   | 8.84    | 11.6    | 11.73   |
| 9  | 3.62    | 2.48    | 7.77    | 10.19   | 8.69    | 8.12    | 7.23    |
| 11 | 4.27    | 3.13    | 8.55    | 10.16   | 9.32    | 9.17    | 9.31    |
| 14 | 5.61    | 3.37    | 8.89    | 10.13   | 8.66    | 8.09    | 8.46    |

Conclusion: Arg. stabilizes FVIII at freezing and TEA stabilizes FVIII during incubation at 4–8° C.

We claim:

1. A mixture comprising fibrinogen, from about 1% to about 20% by weight of 4-(aminomethyl)-cyclohexane-carboxylic acid, and from about 0.1% to about 4% by weight of a co-stabilizer selected from the group consisting of arginine, lysine and a pharmaceutically acceptable salt, thereof.

2. The mixture of claim 1 in an aqueous medium.

3. The mixture of claim 1 further comprising biologically active proteins obtained from blood plasma and, optionally, a buffer.

4. The mixture of claim 1, wherein the amount of tranexamic acid is from about 5% to about 15% by weight and the amount of co-stabilizer is from about 1 to about 3% by weight.

5. The mixture of claim 3, wherein the biologically active proteins are obtained from a cryoprecipitate.

6. The mixture of claim 1, wherein the fibrinogen content is from about 15 to about 150 mg/ml.

7. The mixture of claim 1, further comprising factor VIII, factor XIII, fibronectin, von Willebrand factor, and vitronectin.

8. The mixture of claim 6, wherein the factor VIII, factor XIII, fibronectin, von Willebrand factor, and vitronectin have been prepared by recombinant methods.

9. The mixture of claim 3, wherein the buffer is a glycine buffer.

10. A two component tissue glue comprising separately the components A and B, wherein component A comprises a solution of the mixture of claim 2, and component B comprises a solution of a proteolytic enzyme which is capable of forming fibrin when it reacts with fibrinogen.

11. The two component tissue glue of claim 10, wherein the component B comprises human thrombin in an activity of from about 2 to about 4000 international units per ml.

12. The two component tissue glue of claim 10, wherein component B is stabilized with tranexamic acid and arginine.

13. A fibrin clot obtained by combining the component A and component B of the tissue glue of claim 10.

14. The fibrin clot of claim 13, wherein component A and component B are present at a ratio of 1:1.

* * * * *